United States Patent
Martino et al.

(12)

(10) Patent No.: US 6,210,689 B1
(45) Date of Patent: *Apr. 3, 2001

(54) KERATIN TREATING COSMETIC COMPOSITIONS CONTAINING AMPHOTERIC POLYSACCHARIDE DERIVATIVES

(75) Inventors: Gary T. Martino, Jamesburg; Ian W. Cottrell, Princeton; Manjit S. Chowdhary, Princeton Junction; Kimberly A. Koltai, North Brunswick, all of NJ (US)

(73) Assignee: National Starch & Chemical Co. Investment Holding Corporation, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/040,592

(22) Filed: Mar. 18, 1998

(51) Int. Cl.[7] ................................. A61K 6/00; A61K 7/06
(52) U.S. Cl. ...................... 424/401; 424/70.1; 424/70.11; 424/70.13
(58) Field of Search .................................. 424/401, 70.1, 424/70.11, 70.13

(56) References Cited

U.S. PATENT DOCUMENTS

| | | |
|---|---|---|
| 3,467,647 * | 9/1969 | Benninga et al. .................. 260/209 |
| 3,679,658 | 7/1972 | Yueh et al. ........................ 260/209 R |
| 3,712,883 | 1/1973 | Nordgren ......................... 260/209 R |
| 3,723,409 | 3/1973 | Yueh ................................. 260/209 R |
| 3,740,388 | 6/1973 | Montgomery et al. ........... 260/209 R |
| 3,751,411 | 8/1973 | Elizer ............................... 260/233.3 R |
| 4,088,600 | 5/1978 | Tutein et al. ...................... 252/344 |
| 5,089,252 | 2/1992 | Grollier et al. ................... 424/47 |
| 5,186,928 | 2/1993 | Birtwistle ......................... 424/70 |
| 5,378,830 * | 1/1995 | Yeh .................................. 536/118 |
| 5,387,675 | 2/1995 | Yeh .................................. 536/18.7 |
| 5,536,825 | 7/1996 | Yeh et al. .......................... 536/52 |
| 5,552,462 * | 9/1996 | Yeh .................................. 524/55 |
| 5,573,709 | 11/1996 | Wells ................................ 510/122 |
| 5,733,854 * | 3/1998 | Chowdhary ...................... 510/121 |
| 5,756,720 * | 5/1998 | Chowdhary ...................... 536/124 |

FOREIGN PATENT DOCUMENTS

| | | | |
|---|---|---|---|
| 2 098 226 | 11/1982 | (GB) | ............................ C08L/41/00 |
| 55-45602 | 3/1980 | (JP) | ............................ A61K/7/00 |

* cited by examiner

*Primary Examiner*—Thurman K. Page
*Assistant Examiner*—Isis Ghali
(74) *Attorney, Agent, or Firm*—Laurelee A. Duncan

(57) ABSTRACT

A composition for treating keratin substances comprising selected amphoteric polysaccharide derivatives, preferably guar gum which contain a cationic group comprising an amino, ammonium, imino, sulfonium or phosphonium group and an anionic group comprising a carboxyl, sulfonate, sulfate, phosphate or phosphonate group.

1 Claim, No Drawings

KERATIN TREATING COSMETIC COMPOSITIONS CONTAINING AMPHOTERIC POLYSACCHARIDE DERIVATIVES

BACKGROUND OF THE INVENTION

This invention relates to cosmetic compositions used for treating keratin substances and which contain selected amphoteric polysaccharide derivatives, particularly polygalactomannan derivatives such as guar gum. The resulting compositions have good compatibility as well as being substantive to hair and skin and provide desirable conditioning and aesthetic properties.

Many disclosures of cationic and anionic derivatives of polymers, polysaccharides and polygalactomannans have been made for a variety of applications and uses. Cosmetic compositions containing polymer, polysaccharide and polygalactomannan derivatives for use in treating keratin substances such as hair, skin and nails are also known.

Shampoo compositions containing quaternary ammonium cationic derivatives of galactomannan gum are disclosed in U.S. Pat. No. 5,186,928 issued on Feb. 16, 1993 to D. Birtwistle. U.S. Pat. No. 5,387,675 issued Feb. 7, 1995 to M. Yeh discloses cationic quaternary ammonium ethers of polysaccharides such as starches, celluloses and polygalactomannans as thickening agents in different applications. Cationic organic polymers are disclosed as conditioning agents in hair shampoos in U.S. Pat. No. 5,573,709 issued Nov. 12, 1996 to R. Wells. Cationic starches of the quaternary ammonium type are disclosed as demulsifiers in U.S. Pat. No. 4,088,600 issued May 9, 1978 to T. Tutein et al and Japanese Pat. No. Disclosure 55-45602, published Mar. 31, 1980 to T. Yanagikawa et al. shows cationized hydroxyalkyl starches used in cosmetic compositions.

Anionic carboxyalkyl derivatives of galactomannans have been disclosed in U.S. Pat. No. 3,679,658 issued Jul. 25, 1972 to M. Yueh et al.; U.S. Pat. No. 3,712,883 issued Jan. 23, 1973 to R. Nordgren and U.S. Pat. No. 3,740,388 issued Jun. 19, 1973 to R. Montgomery et al. Carboxyalkyl hydroxyalkyl derivatives of polygalactomannans are disclosed as thickeners in aqueous fluids in U.S. Pat. No. 3,723,409 issued Mar. 27, 1973 to M. Yueh.

Blends of cationic polysaccharides with anionic polysaccharides to produce compositions with enhanced viscosity were disclosed in U.S. Pat. No. 5,378,830 issued on Jan. 3, 1995 to M. Yeh.

U.S. Pat. No. 3,751,411 issued Aug. 7, 1973 to L. Elzier discloses starches containing anionic and cationic groups on the same molecule and which are useful in paper or textile sizing applications.

U.S. Pat. No. 3,467,647 issued Sep. 16, 1969 to H. Benninga shows amphoteric derivatives of polysaccharides containing both cationic and anionic substituents which are useful in producing water-resistant coated paper.

A recent U.S Pat. No. 5,536,825 issued Jul. 16, 1996 to M. Yeh et al. discloses derivatized guar gum having non-ionic, anionic or cationic groups and further exemplifies hydroxyalkyl cationic guar derivatives.

Compositions for treating keratin which comprise cationic and anionic polymers containing vinyl sulfonic groups and synthetic amphoteric polymers as well as amphoteric chitosan derivatives are disclosed in GB Patent No. 2 098 226 published Nov. 17, 1982 to J. Mondal et al.

Another disclosure of keratin treating compositions containing amphoteric polymers is found in U.S. Pat. No. 5,089,252 issued Feb. 18, 1992 to J. Grollier et al. This patent discloses compositions of synthetic amphoteric polymers of betainised dialkylamine alkyl methacrylate or methacrylamide.

Despite the various disclosures of cationic, anionic and amphoteric derivatives as described above, there still is a need for cosmetic keratin treating compositions which are compatible and provide desirable conditioning and aesthetic properties.

SUMMARY OF THE INVENTION

This invention involves a cosmetic composition for treating keratin substances to provide compatibility as well as conditioning and aesthetic properties and which contains selected amphoteric polysaccharide derivatives.

More particularly this invention is directed to a composition for treating keratin substances comprising an amphoteric polysaccharide derivative, preferably amphoteric guar gum derivatives, which contain a cationic group comprising an amino, ammonium, imino, sulfonium or phosphonium group arid an anionic group comprising a carboxyl, sulfonate, sulfate, phosphate or phosphonate group. A particularly preferred keratin treating composition is an amphoteric guar gum derivative containing a tertiary amino or quaternary ammonium ether cationic group and a carboxyalkyl anionic group.

DETAILED DESCRIPTION OF THE INVENTION

The composition of this invention comprises a selected amphoteric polysaccharide derivative containing both a cationic and anionic substituent. The polysaccharide base material may be any of the native or natural polysaccharide polymers obtained from plant, animal and microbial sources. Examples of polysaccharides are starch, cellulose and polygalactomannans and derivatives of each. The polygalactomannans are the preferred polysaccharide and they are composed principally of galactose and mannose units and are usually found in the endosperm of leguminous seeds. Guar, tara and locust bean are illustrative polygalactomannans with guar gum being the preferred polysaccharide.

The polysaccharides are derivatized or modified to contain a cationic group or substituent. The substituted polysaccharides are formed by the derivatization of the hydroxyl functionality of the polysaccharide. The cationic group may be an amino, ammonium, imino, sulfonium or phosphonium group. Such cationic derivatives include those containing nitrogen containing groups comprising primary, secondary, tertiary and quaternary amines and sulfonium and phosphonium groups attached through either ether or ester linkages. The preferred cationic derivatives are those containing the tertiary amino and quaternary ammonium ether groups.

The cationic derivatives as described above may be produced by known methods as disclosed for example in "Cationic Starches", by D. B. Solarek in *Modified Starches: Properties and Uses*, Chapter 8, 1986 and in U.S. Pat. No. 4,119,487 issued Oct. 10, 1978 to M. Tessler. The method for preparing polysaccharides such as starch or guar gum containing tertiary amino groups involves reacting the polysaccharide under alkaline conditions with a dialkylaminoalkyl halide as described in U.S. Pat. No. 2,813,093 issued on Nov. 12, 1957 to C. Caldwell et al. The primary and secondary amine derivatives may be prepared by reacting the polysaccharide with aminoalkyl anhydrides, amino epoxides or halides, or the corresponding compounds containing aryl in addition to the alkyl groups.

Quaternary ammonium groups may be introduced into the guar gum or polysaccharide by treatment with the reaction product of an epihalohydrin and a tertiary amine or tertiary amine salt to provide, for example, 2-hydroxypropyl ether substituent groups as disclosed in the noted U.S. Pat. No. 4,119,487. They may also be introduced into the guar gum by suitable treatment of guar with etherifying agents as described in the previously noted U.S. Pat. No. 2,813,093. The above noted patents, i.e., '487 and '093 are incorporated herein by reference.

The preparation of cationic sulfonium derivatives is described in U.S. Pat. No. 2,989,520 issued June, 1961 to M. Rutenberg et al. and essentially involves the reaction of guar gum or base material in an aqueous alkaline medium with a beta-halogenosulfonium salt, vinylsulfonium salt or epoxyalkyl-sulfonium salt. The preparation of the cationic phosphonium derivatives is disclosed in U.S. Pat. No. 3,077,469 issued Feb. 12, 1963 to A. Aszalos and involves reaction in an aqueous alkaline medium with a beta-halogenoalkylphosphonium salt.

Particularly useful cationic derivatives are those containing amino or nitrogen groups having alkyl, aryl, alkaryl, or cyclic substituents of 1 to 22 carbon atoms and especially alkyl of 1 to 6 carbon atoms.

The polysaccharide used in this invention will also be derivatized with an anionic group or substituent. This anionic group may be a carboxyl, sulfonate, sulfate, phosphate or phosphonate group, preferably a carboxyl group. The introduction of these groups may be achieved by various known methods.

The carboxyl group may be introduced into the polysaccharide by reacting the water-dispersible polysaccharide in the presence of an alkaline catalyst and a mono halogen substituted acid such as monochloro acetic acid, acrylic acid, acrylamide followed by hydrolysis of the amide group and acrylonitrile followed by hydrolysis of the cyanoethyl groups. Carboxyl groups may also be provided by oxidation such as reaction with sodium periodate followed by treatment with sodium chlorite to transform the carbonyl groups to carboxyl groups.

Sulfonate groups can be introduced by reaction with reagents containing functional groups such as sultones, sodium salt of halo alkane sulfonic acids, chloropropane sulfonic acid, epoxypropane sulfonic acid and ethene sulfonic acid. Sulfonate groups may also be introduced by oxidation such as by reaction with sodium periodate followed by treatment with potassium bisulphite. Sulfate groups can be introduced e.g., with addition products of sulfur trioxide and a tertiary amine, or treatment with sulfamic acid and/or sulfuric acid and urea.

Phosphate groups can be added to the polysaccharide by known techniques such as phosphorylation with alkali metal phosphate salts.

The preferred amphoteric derivatives are those containing carboxyl groups as the anionic substituent and more particularly those containing carboxyalkyl groups having from 2 to 6 carbon atoms. The carboxyalkyl ether derivatives are particularly useful and they may be obtained by the reaction of the polysaccharide such as guar gum with a halo alkyl acid containing 2 to 6 carbon atoms or the alkali metal salt thereof. The reaction is carried out using an aqueous alcohol slurry with an alkali metal hydroxide catalyst such as sodium hydroxide. Acids and salts that can be used include monochloroacetic acid and sodium chloroacetate.

The introduction of the anionic and cationic substituents may be carried out either sequentially or simultaneously and the method chosen may depend on the particular reactants, the amount of substituents desired and the method used. Additionally, the amphoteric derivatives used in the compositions of this invention may be prepared in the in-situ continuous alcohol process described in copending application no. 1745, filed on the same date as this application and incorporated herein by reference.

The amount of cationic substituent on the amphoteric polysaccharide will vary between a degree of substitution (DS) of about 0.01 to 1.0, preferably from about 0.1 to 0.6 and more preferably from about 0.2 to 0.5. The amount of anionic substituent will be a DS of from about 0.01 to 1.0, preferably from about 0.1 to 0.6 and more preferably from about 0.2 to 0.5. The preferred amounts of cationic and anionic substituents will be such that there are more or slightly more cationic groups present, that is there is a net positive charge. Stated differently the DS ratio of cationic to anionic groups will be greater than 1, more particularly from greater than 1 up to 100. The term "degree of substitution" (DS) as used herein indicates the average number of sites per anhydroglucose or sugar units (galactose or mannose) on which there are substituent units. The amphoteric polysaccharides as used in this invention may be described as having a total DS, i.e., of both cationic and anionic substituents, of from about 0.2 to 2 and preferably from about 0.3 to 1.2.

The amphoteric polysaccharide derivatives as defined herein are especially useful in cosmetic compositions for the treatment of hair, skin and nails where they provide good compatibility, and substantivity as well as desirable conditioning and aesthetic properties. The use of these amphoteric derivatives and particularly guar gum derivatives in aqueous compositions such as shampoos has been found to provide good clarity resulting in the formation of clear compositions. The keratin treating cosmetic compositions of this invention may involve different media or systems and will comprise a suitable cosmetic vehicle or base for the composition. This vehicle may be an aqueous system, a solvent system, a combination of aqueous and solvent systems or an emulsion. The amphoteric polysaccharide may also be used in personal care products such as dental or toothpaste formulations.

The use of an aqueous system in the cosmetic compositions containing the selected amphoteric polysaccharides in accordance with this invention are found in shampoos, topical sprays, dental care products and products containing fragrances and/or antimicrobial agents. The aqueous system will comprise the selected amphoteric derivative, active additives and functional ingredients, optionally a propellant and the balance water. Generally an aqueous system will comprise from about 10 to 99.8% by weight water, from about 0.1 to 20% of the amphoteric derivative, from about 0.1 to 30% by weight of active additives and ingredients and from about 0 to 50% by weight of propellant. Preferably the composition will comprise 50 to 80% by weight water, 0.2 to 6% by weight of the amphoteric derivative, 0.1 to 20% by weight of active additives and ingredients and 0 to 40% by weight of propellant. For dental care products, the aqueous system will comprise from about 10 to 50% by weight water, from about 0.1 to 10% by weight of amphoteric derivative and from about 40 to 90% by weight of active additives and ingredients Various other additives and active and functional ingredients may be included in the cosmetic composition as defined herein. This includes but is not limited to surfactants, emollients, humectants, thickening agents, UV light inhibitors, preservatives, pigments, dyes, colorants, alpha hydroxy acids, aesthetic enhancers such as starch, perfumes and fragrances, film formers (water proofing agents), antiseptics, antifungal, antimicrobial and other medicaments and solvents. Additionally, the amphoteric polysaccharides as used in this invention may be used in blends with other conditioning polymers and conditioning agents such as cationic hydroxyethyl cellulose, cationic guar, cationic hydroxypropyl guar, cationic synthetic polymers and cationic fatty acid derivatives. These blended materials help to provide more substantivity and effective conditioning properties in hair.

Surfactants which are well known for their use in cosmetic formulations may be added to the compositions of this invention. Such surfactants include but are not limited to alkyl sulfates and alkyl ether sulfates and the salts thereof such as sodium, potassium, ammonium and ethanolamine. Particularly useful surfactants of this type are those having $C_{10}$ to $C_{18}$ alkyl groups. Other suitable anionic surfactants include alkylamidesulfates, alkylamide-ether-sulfates, alkylaryl-polyether-sulfates, monoglyceride-sulfates, alkylsulfonates, alkylamidesulfonates, alkylarylsulfonates, -olefinsulfonates, paraffinsulfonates, alkyl-sulfosuccinates, alkyl-ether-sulfosuccinates, alkylamide-sulfosuccinates, alkyl-sulfosuccinimates, alkyl-sulfoacetates, alkyl-polyglycerolcarboxylates, alkyl phosphates and alkyl-ether phosphates and fatty acids such as oleic, ricinoleic and stearic acid.

Non-ionic and amphoteric surfactants may also be used in the composition of this invention. Non-ionic surfactants which may be used include polyoxyethyleneated, polyoxypropyleneated or polyglycerolated alcohols, alkylphenols and fatty acids with a linear fatty chain containing 8 to 18 carbon atoms and usually 2 to 30 mols of ethylene oxide. Also useful are copolymers of ethylene oxide and propylene oxide, condensates of ethylene oxide and propylene oxide with fatty alcohols, polyoxyethyleneated fatty amides or amines, ethanolamides, fatty acid esters of glycol, oxyethyleneated or non-oxyethyleneated fatty acid esters of sorbitan, fatty acid esters of sucrose, fatty acid esters of polyethylene glycols, phosphoric acid triesters and fatty acid esters of glucose derivatives.

Among the amphoteric surfactants which can be used are alkylamino-monopropionates, alkylaminodipropionates, betaines such as N-alkylbetaines, N-alkylsulfobetaines, n-alkylamidobetaines, cycloimidium compounds such as alkylimidazolines and asparagine derivatives.

Surfactants of the above type are further described and illustrated in U.S. Pat. No. 5,089,252 issued Feb. 18, 1992 to J. Grollier et al.; U.S. Pat. No. 5,186,928 issued Feb. 16, 1993 to D. Birtwistle and U.S. Pat. No. 5,573,709 issued Nov. 12, 1996 to R. Wells. The above noted patents, i.e., '252, '928, and '709 are hereby incorporated by reference.

The topical sprays include the non-aerosol sprays and the aerosol sprays or products containing a propellant. The non-aerosol spray compositions contain no propellant and make use of a mechanical activation device to atomize the composition into a spray. While any of the known propellants may be used in the aerosol compositions of this invention, preferred propellants include the non-halogenated hydrocarbons such as $C_3$–$C_6$ straight and branched chain hydrocarbons, i.e., propane, butane, isobutane and mixtures thereof Other preferred propellants include the ethers, such as dimethyl ether, hydrofluorocarbon and the compressed gases such as $N_2$, $CO_2$.

The use of a solvent system as the vehicle or base involves other cosmetic compositions containing the selected amphoteric polysaccharide derivative. The solvent system will comprise the selected amphoteric derivative, active additives and functional ingredients, optionally a propellant and the balance solvents. The solvent may be any of the known organic solvents which may solubilize or disperse components of the composition and more particularly aliphatic alcohols, esters, ethers, ketones, amines and hydrocarbons including the aromatic, nitrated and chlorinated hydrocarbons. Particularly preferred organic solvents are the lower aliphatic alcohols such as the $C_{1-3}$ alcohols and especially ethanol. Generally the solvent system will comprise from about 25 to 99.8% by weight of solvent, from about 0.1 to 20% by weight of the amphoteric derivative, from about 0.1 to 25% by weight of additives and ingredients and from about 0 to 75% by weight of propellant. Preferably the composition will comprise 50 to 80% by weight of solvent, 0.2 to 6% by weight of amphoteric derivative, 0.1 to 15% by weight of additives and ingredients and 0 to 40% by weight of propellant. The additives and other ingredients and propellants used in the solvent systems are the same as described above for the aqueous systems.

Emulsions may also be used as the vehicle or base for the cosmetic compositions of this invention and products of this type include creams and lotions. These emulsions which comprise water-based and oil-based phases, may be oil-in-water emulsions having oil as the dispersed phase and water as the continuous phase or they may be water-in-oil emulsions with water dispersed in oil, which is the continuous phase. The oil phase, which may comprise from about 10 to 90% by weight of the composition, is typically made up of cosmetically acceptable or conventional oily substances that are soluble in this phase, such as oils, waxes and emulsifiers. Compounds which can be included in the oil phase are typically mineral, animal and vegetable oils and fats, synthetic esters, fatty acids and esters, aliphatic alcohols, higher fatty alcohols, alkyl amines, waxes, so called mineral fats and oils such as paraffin oil, petrolatum, ceresin, silicone oils, silicone fats and fragrances. The water phase may comprise from about 10 to 90% by weight of the composition and this will include water and water soluble components such as alkalis, alkanolamines, polyhydric alcohols and preservatives. These emulsions include one or more emulsifiers which usually are contained in the oil phase but in some instances, depending on the type, may be in the water phase. Emulsifiers which can be used may be ionic or nonionic, are well known and constitute a large group of conventional and commercially available products. They are often characterized by their hydrophilic-lipophilic balance (HLB). Oil-in-water (O/W) emulsifying agents typically have an HLB of more than 6.0 and produce emulsions in which the continuous phase is hydrophilic and such emulsions are generally dispersible in water. Emulsifiers of this type include PEG 300 distearate, sorbitan monolaurate and triethanolamine stearate. Water-in-oil (W/O) emulsifiers usually have an HLB of less than 6.0, preferably below 5, and produce emulsions in which the continuous phase is lipophilic. Such emulsifiers include lanolin, alcohols, ethylene glycol monostearate, sorbitan mono-oleate and PEG 200 dilaurate. Emulsifiers with HLB's of between 5 and 7 may function as either W/O or O/W emulsifiers depending on how they are used.

The amount of emulsifiers used in the emulsion compositions of this invention can vary depending on the system and typically will be an effective emulsifying amount. More particularly, the amount of emulsifier can vary from about 0.1 to 25% by weight of the composition and preferably from about 0.2 to 10%. The emulsion compositions will also contain from about 0.1 to 20% by weight of the amphoteric derivative, preferably from about 0.2 to 6%, and from about 0.1 to 25% by weight of additives and ingredients, preferably 0.1 to 15%. The additives and other ingredients which may be included in the emulsion compositions are the same as those described above for the aqueous systems.

The following examples will further illustrate the embodiments of this invention. In these examples all parts are given by weight and all temperatures in degrees Celsius unless otherwise noted.

EXAMPLE I

A cosmetic shampoo composition was formulated containing an amphoteric guar gum derivative with a hydroxypropyl trimethyl ammonium cationic group (DS of 0.3) and a carboxymethyl anionic group (DS of 0.2) and the following ingredients:

| Ingredients | Parts by weight |
| --- | --- |
| Ammonium lauryl sulfate (30% active) | 25.0 |
| Sodium laureth-2-sulfate (30% active) | 20.0 |
| Cocoamidopropyl betaine (30% active) | 9.62 |
| Lauramide diethanolamine (50% active) | 0.67 |
| Amphoteric guar derivative | 0.5 |
| Deionized water | qs |
| NaCl (to viscosity of 8000 cps) | qs |
| | 100.0 |

The sample had good compatibility and substantivity as well as wet comb properties.

EXAMPLE II

The shampoo composition of Example I as well as similar shampoo compositions which contained the same ingredients, with the amphoteric guar derivative having different amounts of cationic and anionic substituents as indicated by DS were prepared. The sample shampoo formulations were evaluated for clarity using a Hach Turbidity Meter. Results are given in Table 1 below with the turbidity results reported in Ntu.

TABLE 1

| Sample | Additive | Cationic DS | Anionic DS | Turbidity Ntu |
| --- | --- | --- | --- | --- |
| A | Amphoteric guar | 0.3 | 0.2 | 10.9 |
| B | Amphoteric guar | 0.1 | 0.1 | 0.6 |
| C | Amphoteric guar | 0.3 | 0.3 | 6.95 |
| D | Amphoteric guar | 0.45 | 0.3 | 12 |
| E | Amphoteric guar | 0.2 | 0.1 | 9.81 |
| Comparative | Cationic guar (INCI name: guar hydroxypropyltrimonium chloride) | 0.17 | — | 127 |

In the above results, a turbidity value of 15 Ntu or lower is visually clear to the naked eye. The results above show that shampoo compositions containing the amphoteric derivatives in accordance with this invention are essentially clear and transparent as compared to the composition containing the commonly used cationic guar derivative (guar hydroxypropyltrimonium chloride), which has a significantly higher turbidity value and is opaque and non-clear.

EXAMPLE III

Similar shampoo formulations as described and prepared in Examples I and II were prepared and evaluated for excessive buildup. A lumicrease wool dye test was used to determine adsorption and retention of samples containing the amphoteric guar derivatives as compared to a sample containing a cationic polymer and a control blank. The method consists of applying the sample formulations to a wool swatch one (1x) and ten times (10x) and then applying an anionic dye that is attracted to the positively charged polymer film. Through color intensity difference, one can determine the presence of cationic polymer after washing. Color intensity differences were determined with a Technidyne Inc. Brightimeter with lower values representing less polymer adsorption on the substrate. Buildup is characterized after 10x washes by comparing initial and final values. The results are given below in Table 2.

TABLE 2

| Sample | Additive | Cationic DS | Anionic DS | Value 1x wash | Value 10x wash | Difference |
| --- | --- | --- | --- | --- | --- | --- |
| A | Amphoteric guar | 0.3 | 0.2 | 10.00 | 11.13 | +1.13 |
| B | Amphoteric guar | 0.1 | 0.1 | 8.25 | 6.45 | −1.80 |
| C | Amphoteric guar | 0.3 | 0.3 | 6.66 | 5.59 | −1.07 |
| D | Amphoteric guar | 0.45 | 0.3 | 8.34 | 10.22 | +1.88 |
| E | Amphoteric guar | 0.2 | 0.1 | 8.90 | 11.77 | +2.87 |
| Comparative | Cationic guar (guar hydroxypropyl-trimonium chloride) | 0.17 | — | 13.27 | 16.80 | +3.53 |
| Control (Blank) | | | | 0.120 | 0.125 | +0.095 |

The results show less buildup for the compositions containing the amphoteric guar derivatives as compared to one containing a cationic guar derivative i.e., guar hydroxypropyltrimonium chloride.

EXAMPLE IV

Additional shampoo formulations as in Examples I and II were prepared and evaluated for wet comb performance. The wet comb performance was determined quantitatively by applying the test shampoo formulations containing the amphoteric guar derivatives on damaged, blond hair tresses and measuring the resistance in force to pull hair through a comb. The measurement was made using a MTS Systems Inc. Synergie 200 tensile tester. The percent (%) improvement value as shown in the table represents an average of six tresses per sample. The value indicates the difference in force between untreated hair and hair treated with amphoteric guar and rinsed off with water. The results are given in Table 3.

TABLE 3

| Sample | Additive | Cationic DS | Anionic DS | Percentage (%) Improvement* |
| --- | --- | --- | --- | --- |
| A | Amphoteric guar | 0.3 | 0.2 | 42.5 |
| B | Amphoteric guar | 0.1 | 0.1 | 5.4 |
| C | Amphotericguar | 0.3 | 0.3 | 11.9 |
| D | Amphoteric guar | 0.6 | 0.3 | 39.4 |
| E | Amphoteric guar | 0.45 | 0.1 | 28.8 |

*% Improvement compared to untreated wet hair tress

The results show the relative ease of combability for the formulated shampoos containing the amphoteric guar derivatives as represented by comb force % improvement values compared to a wet untreated hair tress.

EXAMPLE V

A baby shampoo composition was formulated with an amphoteric guar derivative having a hydroxypropyl trimethyl ammonium cation group (DS of 0.6) and a carboxymethyl anion group (DS of 0.3) and the following ingredients:

| Ingredients | Parts by weight |
| --- | --- |
| PEG-80 soribitan laurate (32% active) | 50.0 |
| Sodium trideceth sulfate (30% active) | 30.0 |
| Cocoamidopropyl betaine (30% active) | 8.75 |
| Sodium lauroamphodiacetate (32% active) | 12.50 |
| Sodium laureth-13 carboxylate (67% active) | 5.00 |
| Amphoteric guar gum derivative | 0.50 |
| EDTA | 0.13 |
| Citric acid | qs |
| Water | qs |

The sample displayed good compatibility and substantivity as well as wet comb properties.

EXAMPLE VI

A mousse composition was formulated with an amphoteric guar derivative having an hydroxypropyl trimethyl ammonium cation group (DS of 0.1) and a carboxymethyl anion group (DS of 0.3) and the following ingredients:

| Ingredients | Parts by Weight |
| --- | --- |
| Octoxynol-9 | 0.30 |
| Amphoteric guar gum derivative | 1.00 |
| Propylene glycol | 1.00 |
| N-butane/propane | 8.00 |
| Deionized water | 89.70 |

The sample displayed good feel properties, improved stiffness and provided ease of combability on dry and wet hair.

EXAMPLE VII

An amphoteric guar derivative having an hydroxypropyl trimethyl ammonium group (DS of 0.1) and a carboxymethyl anion group (DS of 0.3) was formulated into an oral care application. A toothpaste composition having the following ingredients was prepared:

| Ingredients | Parts by Weight |
| --- | --- |
| Dicalcium phosphate | 47.5 |
| Glycerin (86%) | 30.0 |
| Cellulose Gum | 0.6 |
| Amphoteric guar gum derivative | 0.6 |
| Sodium lauryl sulfate | 1.0 |
| Water | 18.6 |

What is claimed is:

1. A keratin treating cosmetic composition comprising a cosmetic vehicle and from about 0.1 to 20% by weight a guar gum having a cationic group selected from the group consisting of tertiary amino and quarternary ammonium groups and is present in an amount represented by a DS of from about 0.1 to 0.6 and anionic group selected from the group consisting of carboxyl, sulfonate, sulfate, phosphate and phosphonate groups and is present in an amount represented by a DS of from about 0.1 to 0.6 wherein the cosmetic vehicle is an aqueous system and the guar gum has a net positive charge.

* * * * *